(12) United States Patent
Curro

(10) Patent No.: US 6,618,977 B1
(45) Date of Patent: Sep. 16, 2003

(54) METHOD AND DEVICE FOR HARVESTING EARTHWORMS

(76) Inventor: Santo J Curro, 517 Clinton St., Horicon, WI (US) 53032

( * ) Notice: Subject to any disclaimer, the term of this patent is extended or adjusted under 35 U.S.C. 154(b) by 0 days.

(21) Appl. No.: 10/113,366

(22) Filed: Mar. 29, 2002

(51) Int. Cl.[7] ............................................... A01M 7/00
(52) U.S. Cl. ............................. 43/1; 239/310; 239/302
(58) Field of Search ............................... 43/1; 239/310, 239/313

(56) References Cited

U.S. PATENT DOCUMENTS

| | | | |
|---|---|---|---|
| 317,634 A | * 5/1885 | Ernst | 4/226.1 |
| 563,195 A | 6/1896 | Lyon | |
| 647,411 A | * 4/1900 | Jenkins | 137/624.13 |
| 1,446,914 A | 2/1923 | Lingafelter | |
| 1,469,065 A | 9/1923 | D'Arcy | |
| 1,981,623 A | 11/1934 | Karter | |
| 2,064,178 A | 12/1936 | Pickard | |
| 2,156,114 A | 4/1939 | Gilford | |
| 2,481,279 A | 9/1949 | Barr | |
| 3,199,957 A | 8/1965 | Vivion | |
| 3,239,413 A | 3/1966 | Chaney | |
| 3,615,244 A | * 10/1971 | Long et al. | 222/630 |
| 3,761,021 A | 9/1973 | White | |
| 4,178,711 A | 12/1979 | Mermal et al. | |
| 4,556,679 A | 12/1985 | Koehler | |
| 4,570,372 A | 2/1986 | Lukas | |
| 4,634,053 A | 1/1987 | Herzfeld et al. | |
| 4,785,850 A | * 11/1988 | Sanchez | 137/894 |
| 4,934,087 A | 6/1990 | Zanon et al. | |
| 5,301,633 A | 4/1994 | Lloyd | |
| 5,524,375 A | 6/1996 | Morrison | |
| 6,241,164 B1 | 6/2001 | Wolfe | |

FOREIGN PATENT DOCUMENTS

| | | |
|---|---|---|
| CA | 1174968 | 4/1982 |
| GB | 464244 | 4/1937 |

* cited by examiner

*Primary Examiner*—Charles T. Jordan
*Assistant Examiner*—Bret Hayes
(74) *Attorney, Agent, or Firm*—Ryan Kromholz & Manion, S.C.

(57) ABSTRACT

A method and device for causing earthworms to emerge from ground soil for harvesting, including providing a spraying device, having an inlet, an outlet, and a mixing chamber located intermediate the inlet and the outlet, wherein the mixing chamber is arranged to receive a worm lure composition for mixing with a mixing fluid coupled to the inlet to thereby provide a worm lure mixture, spraying the mixture from the outlet onto ground soil containing worms thereby causing worms to emerge from the ground soil, and collecting the worms. The device includes an inlet, an outlet, and a mixing chamber for mixing a worm lure composition with mixing fluid.

11 Claims, 6 Drawing Sheets

METHOD AND DEVICE FOR HARVESTING EARTHWORMS

BACKGROUND OF THE INVENTION

This invention relates to a method and device for encouraging earthworms, particularly night crawlers, to emerge from their burrows for harvest.

Presently, fishermen and others requiring night crawlers, use lights to find worms as they emerge at night. This method is time consuming and yields uneven results. The present invention allows the user to quickly and accurately locate and capture worms, particularly night crawlers, at any time of the day or night, in various weather conditions, at any location having ground soil containing earthworms.

It is presently known to use chemical compounds or electrical current to cause earthworms to emerge from their burrows. U.S. Pat. No. 4,570,372, for example, discloses a worm harvesting method, which comprises wetting ground soil with an aqueous solution containing free chlorine. The method includes forming the solution in a pail and continually flowing water into the pail so that the solution overflows the confines of the pail and pours on the ground surrounding the pail. While this method may yield some positive result, the rate of water flowing out of the pail is difficult to control. Further, the user is limited to application of the solution to the area immediately surrounding the pail. Since not all ground soil contains earthworms, if the area surrounding the pail is found not to contain earthworms, the user must transfer the pail and solution therein to other sites in succession until an earthworm-containing site is located. This is inconvenient and time-consuming for the user.

The present method and apparatus for harvesting earthworms includes an easily used fluid mixer. The method includes controllably wetting ground soil containing earthworms with an aqueous solution containing at least 10 parts per million of free chlorine. The solution is mixed in the mixing chamber of the novel fluid mixer and sprayed out the discharge end. The method allows the user to readily move from one harvest area to another and provides a solution that minimizes damage to the flora and fauna in the harvesting area. The apparatus comprises a spraying device having an inlet, an outlet, and a mixing chamber.

SUMMARY OF THE INVENTION

The present invention provides an improved method for causing earthworms to come out of the ground so that they may be readily harvested, and also provides a device for use in mixing a fluid composition functional when applied to ground soil containing earthworms to cause the earthworms in the ground soil to emerge for harvesting.

The method of the present invention generally comprises the steps of: 1. Providing a predetermined amount of a worm lure composition. 2. Providing a spraying device, having an inlet, an outlet, and a mixing chamber located intermediate said inlet and said outlet; the mixing chamber arranged to receive the predetermined amount of worm lure composition. 3. Providing a source of pressurized mixing fluid coupled to the inlet. 4. Providing a fluid passageway communicating with the inlet and mixing chamber. 5. Mixing the mixing fluid and the predetermined amount of worm lure composition in the mixing chamber to provide a worm lure mixture having at least 10 parts per million chlorine. 6. Providing a second fluid passageway, the second fluid passageway communicating with the outlet and the mixing chamber. 7. Spraying the worm lure mixture from the outlet onto ground soil containing worms thereby causing worms to emerge from the ground soil. B. Collecting the worms.

The worm lure mixture used in the present invention is generally comprised of an aqueous solution having at least 10 parts per million chlorine, as mixed in the mixing chamber of the novel fluid mixer. The fluid mixer includes an inlet and an outlet. The inlet is adapted to be attached to a conventional water supply hose, such as a garden hose. The inlet and outlet each include a passageway bore having a predetermined diameter. The inlet bore communicates with a pellet or mixing chamber which is adapted to receive worm lure composition, such as a pellet or tablet containing a predetermined amount of available chlorine. The bore of said first passageway transversely intersects the bore of the mixing chamber at a point intermediate the ends of the mixing chamber bore, and further, one end of the mixing chamber bore transversely intersects the inner end of the second passageway bore. The pellet or mixing chamber includes a first aperture communicating with the inlet bore and a second aperture communicating with an outlet bore. The outlet bore includes a distal discharge outlet. It is preferred that the inlet bore be of a larger diameter than the outlet bore to thereby provide increased resistance for the fluid. flow through the device.

The pellet or mixing chamber is further provided with a pellet insert opening including a threaded cap. The pellet or mixing chamber may also include a tubular insert spacer to assist in retaining an inserted pellet in place. In one embodiment, the chamber spacer may be provided with at least one aperture to allow water flowing through the inlet bore to enter the chamber, flush over the pellet to dissolve the pellet, and exit as a worm lure solution through the discharge bore. The solution exits the discharge bore and is sprayed on ground soil at a worm-collecting site. As the solution is applied to the ground soil or turf, it comes in contact with worms. The solution encourages the worms to come to the surface of the soil for easy capture and collection. It is noted that this method may be practiced with good results during the day or night, and in any temperate weather condition. Further, worms harvested by this method are not harmed by the worm lure mixture and may be stored in any conventional manner after being rinsed in water.

DETAILED DESCRIPTION

Figure 1:
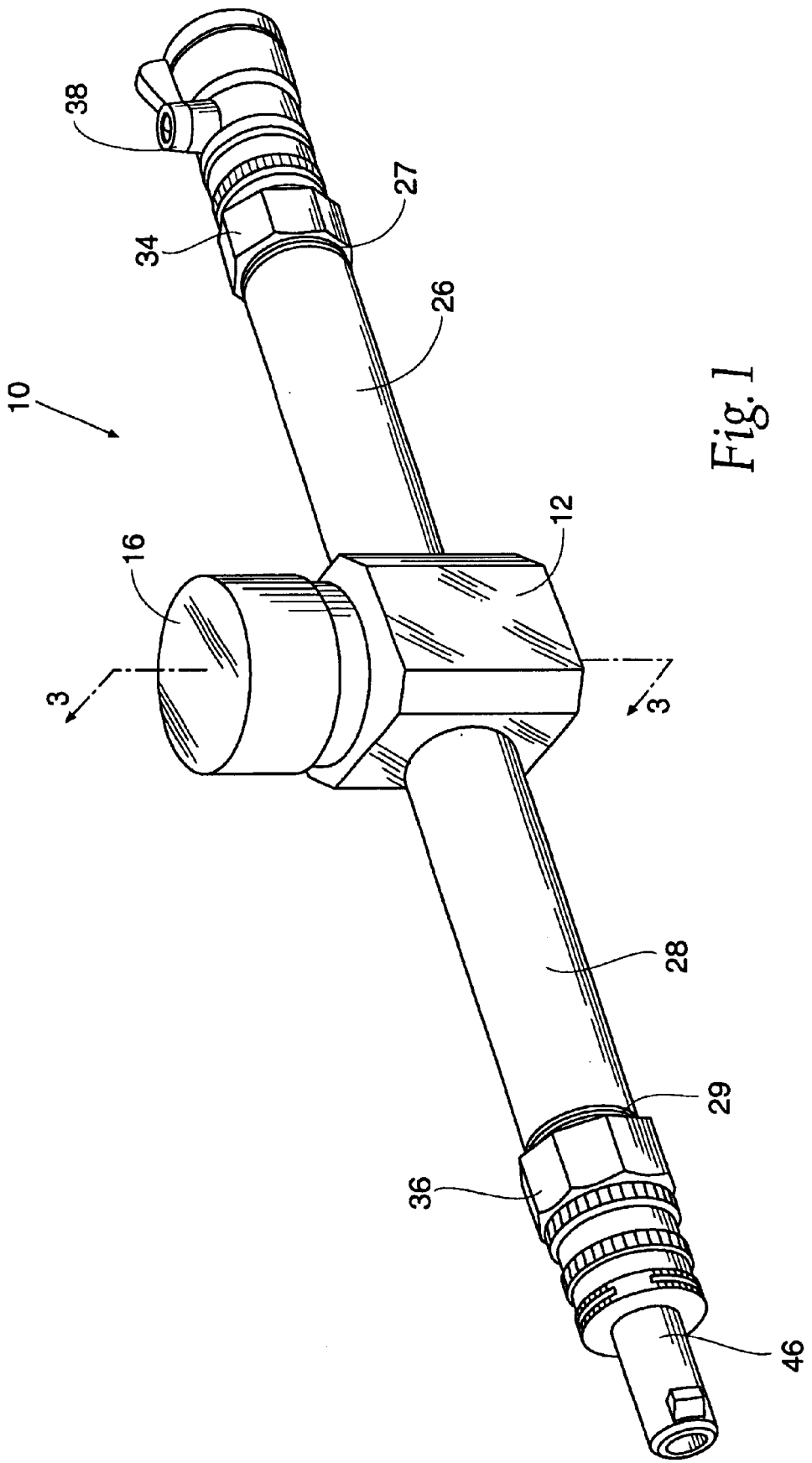
FIG. 1 is a perspective view of one embodiment of the invention.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The method of the present invention generally comprises the steps of: 1. Providing a predetermined amount of a worm lure composition. 2. Providing a spraying device, having an inlet, an outlet, and a mixing chamber located intermediate said inlet and said outlet; the mixing chamber arranged to receive the predetermined amount of worm lure composition. 3. Providing a source of pressurized mixing fluid coupled to the inlet. 4. Providing a fluid passageway communicating with the inlet and mixing chamber. 5. Mixing the mixing fluid and the predetermined amount of worm lure composition in the mixing chamber to provide a worm lure mixture. 6. Providing a second fluid passageway, the second fluid passageway communicating with the outlet and the mixing chamber. 7. Spraying the worm lure mixture from the outlet onto ground soil containing worms thereby causing worms to emerge from the ground soil. 8. Collecting the worms.

The spraying device of this invention is illustrated and described herein in connection with two embodiments and is indicated generally by the reference numeral 10. The first embodiment is best described in connection with the views of FIGS. 1, 3, and 5 wherein the spraying device 10 may be injection molded as an integrally formed device comprising a mixing, or pellet chamber 12 including a tubular bore 14 (seen in FIG. 3). The pellet chamber 12 is open at its, upper end 15 and externally threaded to receive a removable closure cap 16 for insertion of a frusto-conical particulate screen member 18 seated on the inner, shouldered end 20 of the bore 14. The screen member 18 is held in place by a tubular insert 22 forced towards the member 18 by the threaded closure cap 16. The insert is 22 preferably positioned after placement of a desired number of pellets 24 (shown in phantom) containing worm lure composition in the chamber 12.

Suitable worm lure compositions are preferably in pellet or tablet form having a predetermined density and further providing a predetermined amount of available chlorine. The preferred density being that which allows adequate erosion of the tablet in the chamber 12 over a period of 40–50 minutes at a water flow rate of about two gallons minute, to provide an exiting worm lure mixture having at least 10 parts per million available chlorine. Some examples of preferred worm lure compositions are as follows: One-fourth ounce tablets, or pellets, each containing 68% available chlorine in the form of Calcium Hypochlorite and 32% inert ingredients, dry weight. Pellets of this type may be obtained from Arch Chemical Inc. of Norwalk, Conn. Another suitable example was found to be tablets containing 56% available chlorine in the form of Trichloro-S-triazinetrione, wherein the tablet contains 67% Trichloro-S-triazinetrione and 33% Sodium carbonate by weight. While the worm lure mixture may be formed using the above-mentioned pellets, it is to be understood that a suitable worm lure mixture may be obtained using other solid or granular worm lure compositions which provide a controlled release of free chlorine.

Figure 3:
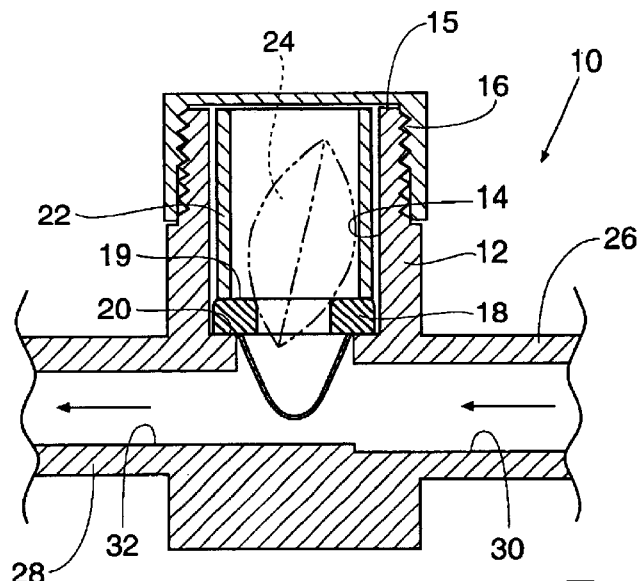
FIG. 3 is a fragmentary cross sectional view of the embodiment illustrated in FIG. 1 and taken along lines 3—3 thereof.
Figure 5:
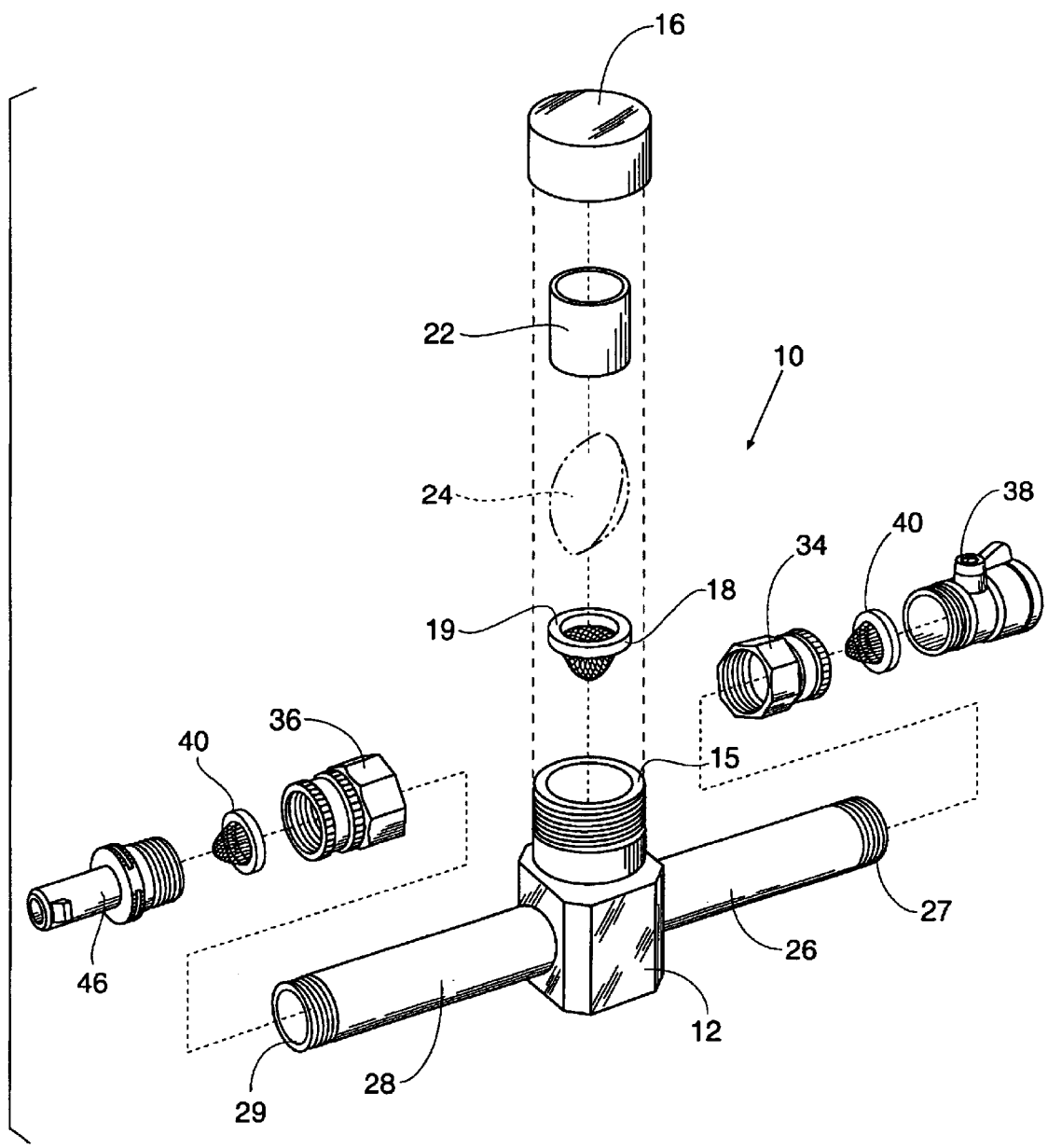
FIG. 5 is a partially exploded view of the device illustrated in FIGS. 1 and 3.

The mixing chamber portion 12 of the embodiment of FIGS. 1, 3 and 5 is preferably integrally formed with laterally extending inlet and outlet arm portions or fluid passageways 26 and 28. As best seen in FIG. 3, the arm portions 26, 28 each respectively contain tubular bores 30 and 32. The bore 30 of arm 26 transversely intersects the bore 14 of the mixing chamber 12 at a point intermediate the ends of the mixing chamber bore 14. Further, one end of the mixing chamber bore 14 transversely intersects the inner end of the second arm bore 32. It is preferred that the inlet bore 30 have a larger diameter than the outlet bore 32, to thereby provide increased resistance for the fluid flow through the spraying device 10. This flow resistance acts to provide turbulence which assists in thorough mixing of the lure composition 24 with fluid flowing through the device 10, thereby permitting maximum efficiency and increased spreading of the resultant worm lure mixture on ground soil, and maximum collection of earthworms. The aforementioned turbulence acts to rapidly agitate the worm lure composition pellet(s) 24 in the mixing chamber 12, and erode them for desired suspension and mixing with the fluid flowing through the spraying device 10. It will be apparent that the device 10 provides fluid passage through the inlet bore 30, the mixing chamber bore 14, and outwardly of the outlet bore 32 to a suitable nozzle 46 threadingly engaging the outlet arm 28. (Seen in FIGS. 1 and 5).

Figure 7:
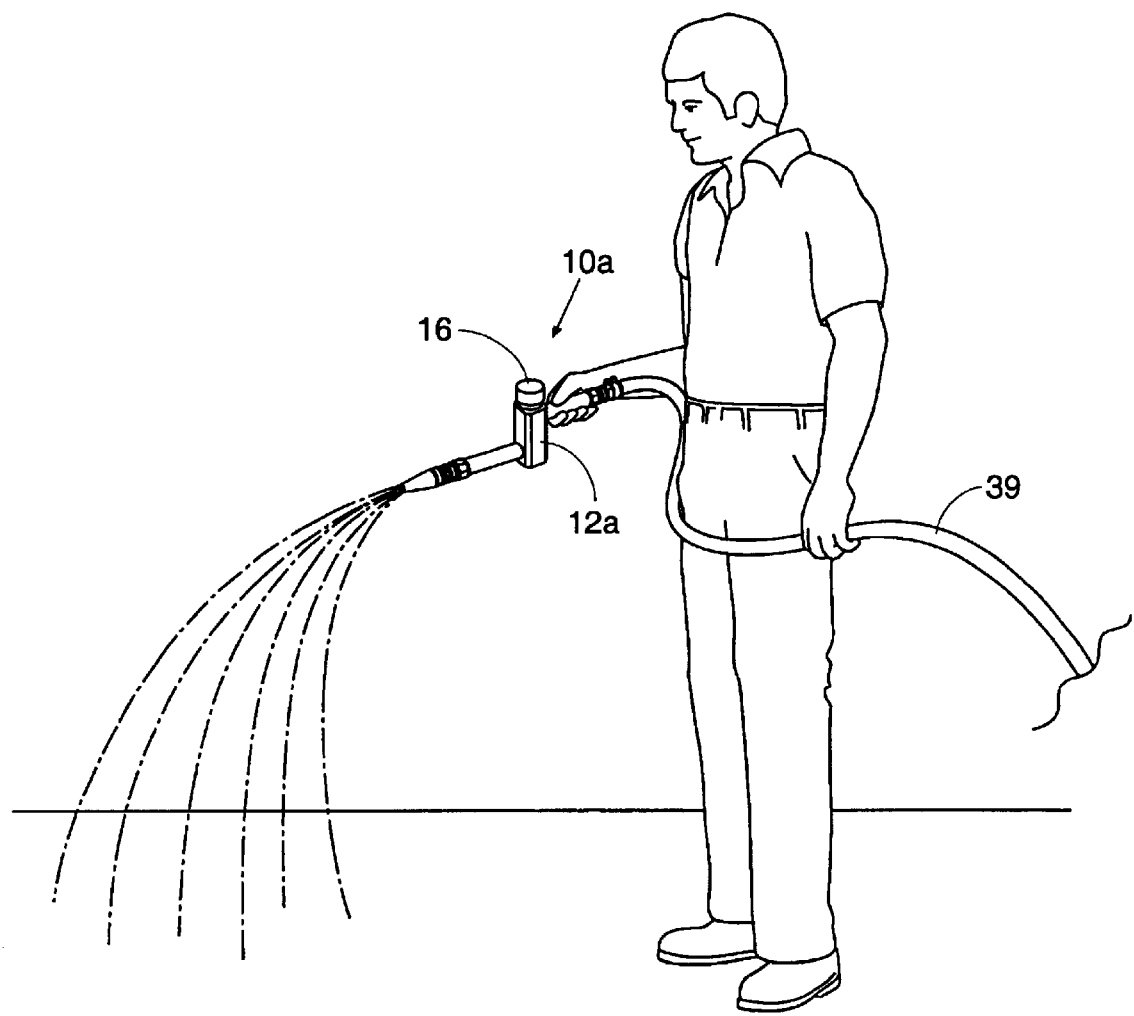
FIG. 7 illustrates the device of FIGS. 2, 4, and 6 as used for causing earthworms to emerge from ground soil.

As seen particularly in FIG. 5, it will be noted that the inlet end 27 of inlet arm 26 is preferably threaded to receive a conventional inlet coupling 34, and the outlet end 29 of outlet arm 28 is preferably threaded to receive an outlet coupling 36. A control valve 38 is provided at the inlet end 27 to control incoming mixing fluid flow rate. The inlet coupling 34 is preferably adapted to be attached to a conventional water supply hose, such as a garden hose 39, as seen in FIG. 7. Further, and as seen in FIG. 5, it is preferable that the inlet and outlet ends 27, 29 each be provided with respective screen inserts 40 to prevent large particles from entering or exiting the device 10.

Figure 2:
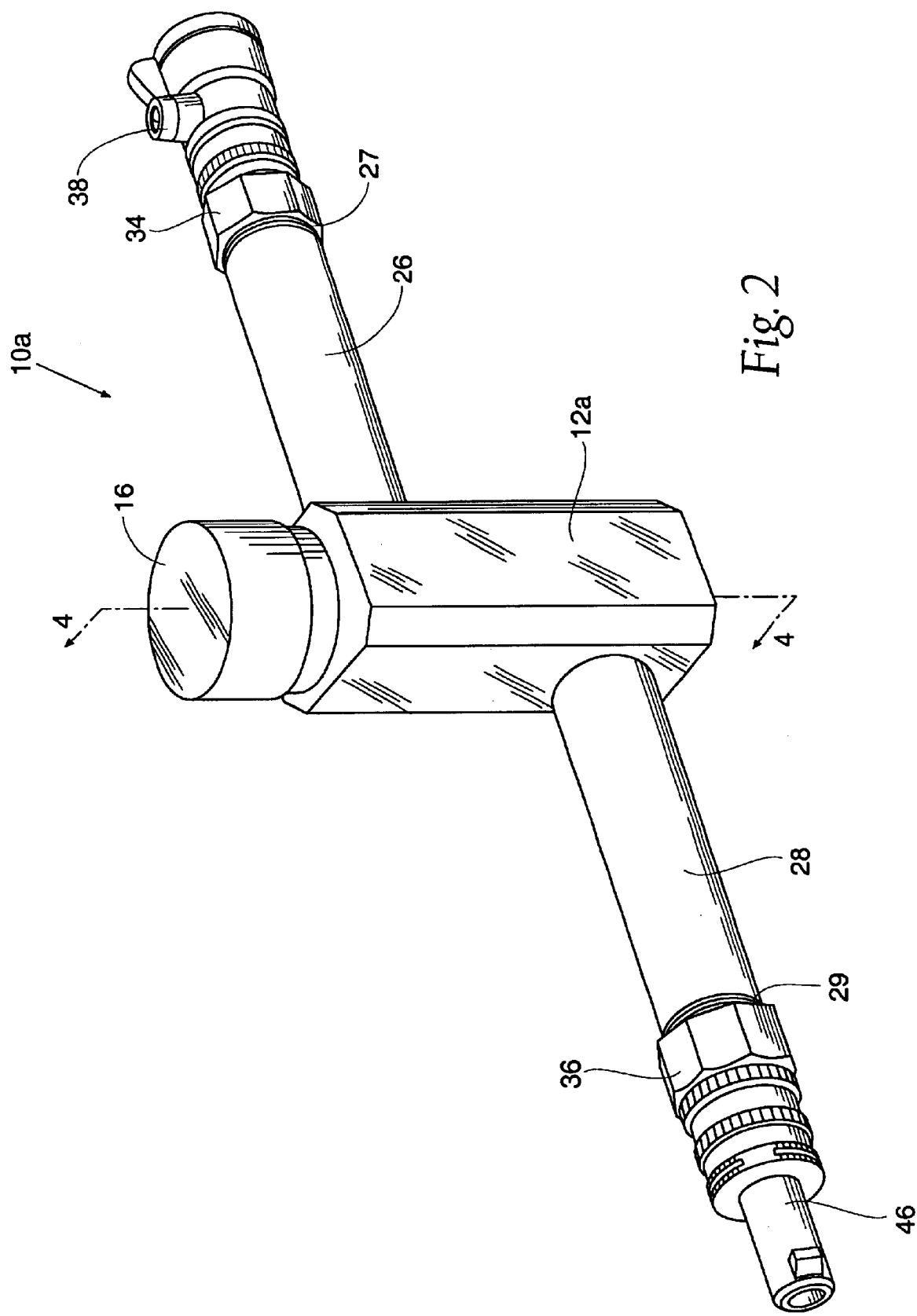
FIG. 2 is a perspective view of an alternative embodiment of the invention.
Figure 4:
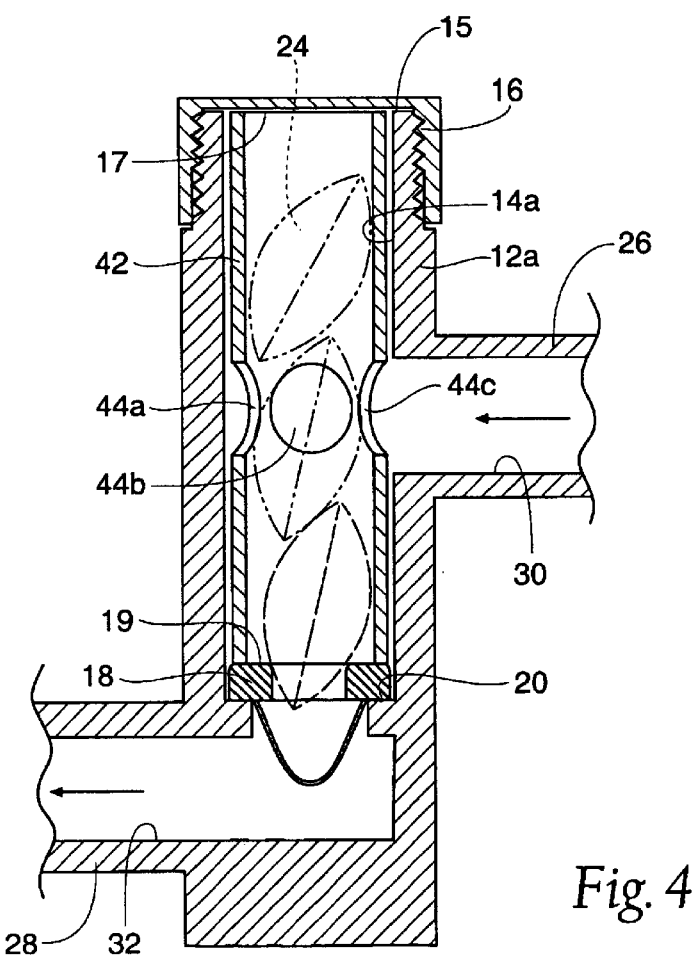
FIG. 4 is a fragmentary cross sectional view of the embodiment illustrated in FIG. 2 and taken along lines 4—4 thereof.
Figure 6:
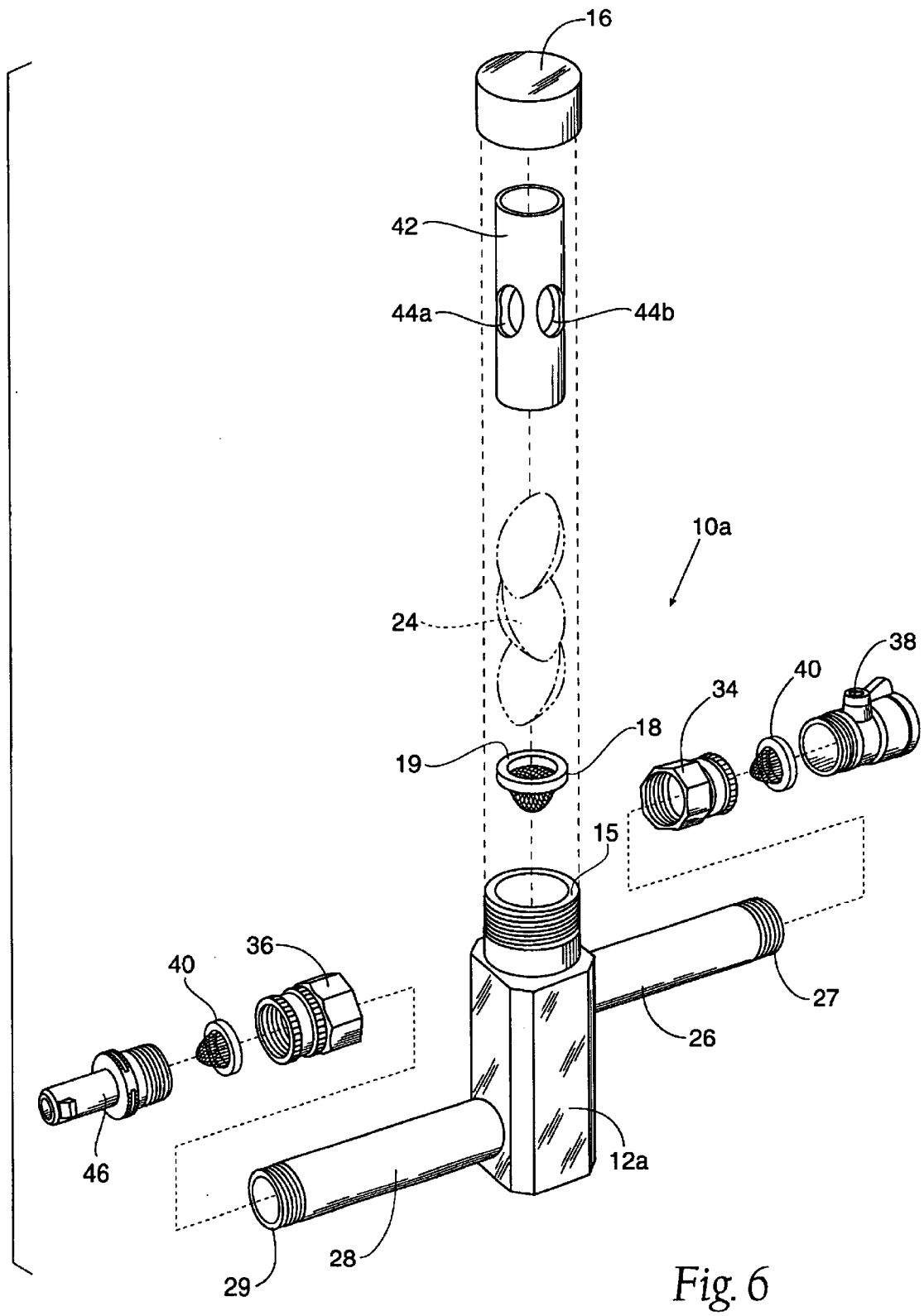
FIG. 6 is a partially exploded view of the device illustrated in FIGS. 2 and 4.

As previously mentioned, another embodiment of the invention is illustrated in the views of FIGS. 2, 4 and 6. This embodiment includes a modified mixing chamber 12a, wherein it will be noted that the length of the mixing chamber 12a has been extended relative to the length of the mixing chamber 12 seen in FIGS. 1, 3 and 5. This alternative configuration permits insertion of a tubular insert 42 having increased length, thereby allowing a plurality of openings 44a, 44b and 44c to be formed therein. The openings 44a, 44b, 44c permit more thorough agitation of the pellet(s) 24 and aid in mixing of the pellet composition with fluid flowing through the device 10a.

Similarly to the first embodiment described, the alternative embodiment spraying device 10a seen in FIGS. 2, 4, and 6, may be injection molded as an integrally formed device. The alternative embodiment device 10a further comprises a modified mixing, or pellet chamber 12a including an extended tubular bore 14a, as seen in FIGS. 4 and 6. The pellet chamber 12a is open at its upper end 15 and externally threaded to receive a removable closure cap 16 for insertion of a frusto-conical particulate screen member 18 seated on the inner, shouldered end 20 of the bore 14. The screen member 18 is held in place by a tubular insert 42 having increased length, which is forced towards the member 18 by the threaded closure cap 16. The insert 42 is preferably positioned after placement of a desired number of pellets 24 (shown in phantom) containing worm lure composition in the chamber 12. The tubular insert 42 is held in place between the inner surface 17 of the removable cap 16 and the rim 19 of the particulate screen 18. The screen 18 in turn rests upon the shoulder 20.

As in the previous embodiment, the modified mixing chamber portion 12a of the embodiment of FIGS. 2, 4, and 6 is preferably integrally formed with laterally extending inlet and outlet arm portions 26 and 28. As best seen in FIG. 4, the arm portions 26, 28 each respectively contain tubular bores 30 and 32. As stated earlier with regard to FIGS. 1, 3, and 5, it is preferred that the inlet bore 30 have a larger diameter than the outlet bore 32, to thereby provide increased resistance and turbulence for the fluid flow through the spraying device 10a. It will be apparent that the device 10a provides fluid passage through the inlet bore 30, the mixing chamber bore 14a, and outwardly of the outlet bore 32 to a suitable nozzle 46 threadingly engaging the outlet arm 28. (Seen in FIGS. 2 and 6).

As noted with reference to the previous embodiment, and as seen particularly in FIG. 6, the inlet end 27 of inlet arm 26 is preferably threaded to receive a conventional inlet coupling 34, and the outlet end 29 of outlet arm 28 is preferably threaded to receive an outlet coupling 36. A control valve 38 is provided at the inlet end 27 to control incoming mixing fluid flow rate. The inlet coupling 34 is preferably adapted to be attached to a conventional water supply hose, such as a garden hose 39, as seen in FIG. 7. Further, and as seen in FIG. 6, it is preferable that the inlet and outlet ends 27, 29 each be provided with respective screen inserts 40 to prevent large particles from entering or exiting the device 10a.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A method of harvesting worms from ground soil contain worms, comprising the steps of:
    providing a source of pressurized water;
    providing a predetermined amount of a worm lure composition comprised of at least 65% by weight of calcium hypochlorite and 35% by weight of inert ingredients capable of producing at least 68% available chlorine when mixed with water delivered from said water source;
    providing a spraying device, said spraying device including an inlet, an outlet, and a mixing chamber for mixing said composition with said pressurized water, said mixing chamber being located intermediate said inlet and said outlet; said mixing chamber having a shouldered inner end and an outer end and being arranged to receive said predetermined amount of worm lure composition;
    providing a source of pressurized water, said source of pressurized water being coupled to said inlet;
    providing a fluid passageway communicating with said inlet and said mixing chamber;
    mixing said water and said predetermined amount of worm lure composition in said mixing chamber to nearly instantly provide a worm lure mixture;
    providing a second fluid passageway, said second fluid passageway communicating with said outlet and with said mixing chamber,
    spraying said worm lure mixture from said outlet to said ground soil containing worms; causing said worms to emerge from said ground soil; and
    collecting said worms.

2. The method of claim 1 wherein said available chlorine is derived from a mixture of an inert ingredient and an active ingredient, and wherein the active ingredient is selected from the group consisting of Calcium hypochlorite, Trichloro-S-triazinetrione, and Sodium dichlor-s-triazinetrione anhydrous.

3. The method of claim 1 wherein said worm lure mixture provides at least 10 parts per million of chlorine.

4. A spraying device for applying a worm lure mixture to ground soil containing earthworms, said spraying device comprising:
    an inlet, an outlet, and a mixing chamber located intermediate said inlet and said outlet, said mixing chamber having a shouldered inner end and an outer end and being arranged to receive a predetermined amount of a worm lure composition;
    said inlet being adapted to be coupled to a source of pressurized mixing fluid;
    a first fluid passageway arranged for communication with said inlet and with the shouldered inner end of said mixing chamber,
    said mixing chamber being adapted for mixing said mixing fluid and said predetermined amount of worm lure composition, thereby providing a predetermined amount of a worm lure mixture
    a second fluid passageway, said second fluid passageway communicating with said outlet and with the inner end of said mixing chamber;
    said mixing chamber and each of said first and second fluid passageways comprising a tubular bore, and wherein the bore of said first passageway transversely intersects the bore of said mixing chamber at a point intermediate the ends of said mixing chamber bore, and further, wherein one end of said mixing chamber bore transversely intersects the inner end of said second passageway bore; and
    a flanged frusto-conical screen located within said mixing chamber and with its flange being supported by said shouldered inner end and being arranged to provide lateral support to said worm lure composition before and during exposure to said mixing fluid;
    a tubular insert received by said mixing chamber and having one end resting on the flange of said frusto-conical screen and the opposite end of said insert being arranged for contact with said closure member and for forcing said screen towards supporting engagement with said shouldered inner end of said mixing chamber during closure of said closure member with respect to the outer end of said mixing chamber;
    an inlet screen insert transversely positioned at said inlet for preventing entrance of particulate mater of predetermine size; and
    an outlet screen insert transversely positioned at said outlet for controlling particulate size of mixed worm lure composition exiting said spraying device;
    said outlet being adapted to spray said worm lure mixture on said ground soil containing earthworms.

5. The device of claim 4 wherein said worm lure composition provides at least 68% available chlorine.

6. The device of claim 5 wherein said available chlorine is derived from a of an inert ingredient and an active ingredient, and wherein the active ingredient is selected from the group consisting of Calcium hypochlorite, Trichloro-S-triazinetrione, and Sodium dichlor-s-triazinetrione anhydrous.

7. The spraying device of claim 4, wherein said first fluid passageway and said second fluid passageway each comprise tubular bores and the diameter of the first fluid passageway bore is larger than the diameter of the second fluid passageway bore.

8. The device of claim 4 wherein said pressurized mixing fluid consists of water.

9. The device of claim 4 wherein said worm lure mixture provides at least 10 parts per million of chlorine.

10. The device of claim 5 wherein said inlet is provided with respective water fluid flow control means.

11. The device of claim 10 wherein said fluid flow control means consists of a control valve.

* * * * *

UNITED STATES PATENT AND TRADEMARK OFFICE
CERTIFICATE OF CORRECTION

PATENT NO. : 6,618,977 B1
DATED : September 16, 2003
INVENTOR(S) : Curro

It is certified that error appears in the above-identified patent and that said Letters Patent is hereby corrected as shown below:

<u>Column 6,</u>
Line 48, delete "mater" and insert -- material --
Line 58, delete "from a of" and insert -- from a mixture of --

Signed and Sealed this

Twentieth Day of April, 2004

JON W. DUDAS
*Acting Director of the United States Patent and Trademark Office*